United States Patent [19]
Metelev et al.

[11] Patent Number: 6,143,881
[45] Date of Patent: *Nov. 7, 2000

[54] HYBRID OLIGONUCLEOTIDE PHOSPHOROTHIOATES

[75] Inventors: Valeri Metelev, Moscow, Russian Federation; Sudhir Agrawal, Shrewsbury, Mass.

[73] Assignee: University of Massachusetts Worcester, Worcester, Mass.

[*] Notice: This patent is subject to a terminal disclaimer.

[21] Appl. No.: 08/476,082

[22] Filed: Jun. 7, 1995

Related U.S. Application Data

[63] Continuation of application No. 07/918,238, Jul. 23, 1992, Pat. No. 5,275,201.

[51] Int. Cl.[7] .......................... C07H 21/04; A01N 43/04; A01N 59/26

[52] U.S. Cl. .......................... 536/24.5; 514/44; 536/23.1; 536/25.3; 536/25.33; 536/25.7; 424/601

[58] Field of Search .......................... 514/44; 536/24.5, 536/25.3, 25.33, 23.1, 25.7; 424/601; 935/2, 8, 36

[56] References Cited

U.S. PATENT DOCUMENTS

| | | | |
|---|---|---|---|
| 4,689,320 | 8/1987 | Kaji | 514/44 |
| 4,806,463 | 2/1989 | Goodchild et al. | 435/5 |
| 4,908,307 | 3/1990 | Rodland et al. | 435/6 |
| 5,013,830 | 5/1991 | Ohtsuka et al. | 536/27 |
| 5,015,570 | 5/1991 | Scangos et al. | 435/6 |
| 5,107,065 | 4/1992 | Shewmaker et al. | 800/205 |
| 5,134,066 | 7/1992 | Rogers et al. | 435/91 |
| 5,149,797 | 9/1992 | Pederson et al. | 536/27 |
| 5,149,798 | 9/1992 | Agrawal et al. | 536/27 |
| 5,194,428 | 3/1993 | Agrawal et al. | 514/44 |
| 5,220,007 | 6/1993 | Pederson et al. | 536/23.1 |
| 5,478,369 | 12/1995 | Albertsen et al. | 47/58 |
| 5,591,721 | 1/1997 | Agrawal et al. | 514/44 |
| 5,652,355 | 7/1997 | Metelev et al. | 536/24.5 |

FOREIGN PATENT DOCUMENTS

| | | | |
|---|---|---|---|
| 2017369 | 11/1990 | Canada | C07F 7/24 |
| 0260032 | 3/1988 | European Pat. Off. | C07H 21/00 |
| 0339330 | 11/1989 | European Pat. Off. | C07C 69/14 |
| 0339842 | 11/1989 | European Pat. Off. | C07H 21/00 |
| 3915462 | 9/1990 | Germany | C07H 19/167 |
| 4110085 | 10/1992 | Germany | C07H 19/20 |
| 3240795 | 10/1991 | Japan | C07H 21/00 |
| WO 89/05358 | 6/1989 | WIPO . | |
| WO9015814 | 12/1990 | WIPO | C07H 21/04 |
| WO9106556 | 5/1991 | WIPO | C07H 21/00 |
| WO9112323 | 8/1991 | WIPO | C12N 15/10 |
| WO 91/15500 | 10/1991 | WIPO | C07H 21/00 |
| WO9115499 | 10/1991 | WIPO | C07H 19/04 |
| WO9207065 | 4/1992 | WIPO | C12H 9/00 |
| WO 92/20697 | 11/1992 | WIPO . | |
| WO9313121 | 7/1993 | WIPO | C07H 21/00 |

OTHER PUBLICATIONS

Uhlmann et al. "Antisense Oligonucleotides: A New Therapeutic Principle" Chemical Reviews, vol. 90, No. 4, pp. 543–584, Jun. 1990.

Shibahara et al. "Site–Directed cleavage of RNA" Nucleic Acids Research, vol. 15, pp. 4403–4415, 1987.

Agrawal and Tang, *Tetrahedron Lett.* 31, 1543–1546 (1990).

Agrawal et al. *Proc. Natl. Acad. Sci USA* 85, 7079–7083 (1988).

Agrawal et al., *Biochem. Pharmacol.* 50 (4), 571–576 (1995).

(List continued on next page.)

*Primary Examiner*—Jezia Riley
*Attorney, Agent, or Firm*—McDonnell Boehnen Hulbert & Berghoff

[57] ABSTRACT

The invention provides hybrid oligonucleotides having phosphorothioate or phosphorodithioate internucleotide linkages, and both deoxyribonucleosides and ribonucleosides or 2'-substituted ribonucleosides. Such hybrid oligonucleotides have superior properties of duplex formation with RNA, nuclease resistance, and RNase H activation.

53 Claims, 4 Drawing Sheets

OTHER PUBLICATIONS

Agrawal et al., *Nucleosides & Nucleotides* 8, 819–823 (1989).
Agrawal et al., *Proc. Natl. Acad. Sci USA* 86, 7790–7794 (1989).
Agrawal et al., *Proc. Natl. Acad. Sci USA* 87, 1401–1405 (1990).
Agrawal, *Tibtech* 10, 152–158 (1992).
Agris et al., *Biochem* 25, 6268–6275 (1986).
Atabekov et al., *FEBS Lett.* 232, 96–98 (1988).
Birg et al., *Nucleic Acids Res.* 18, 2901–2908 (1990).
Brill et al., *J. Amer. Chem. Soc.* 113, 3972–3980 (1991).
Campbell et al., *Nature* 311, 350–355 (1984).
Cooney, *Science,* vol. 241, pp. 456–459, Jul. 22, 1988.
Dagle et al., *Antisense Res. Dev.* 1, 11–20 (1991).
Dagle et al., *Nucleic Acids Res.* 18, 4751–4757 (1990).
Dagle et al., *Nucleic Acids Res.* 19, 1805–1810 (1991).
Davison and Scott, *J. Gen. Virol.* 67, 2279–2286 (1986).
Eder and Walder, *J. Biol. Chem.* 266, 6472–3479 (1991).
Furdon et al., *Nucleic Acids Res.* 17, 9193–9204 (1989).
Gao et al., *Antimicrob. Agents and Chem.* 34, 808–812 (1990).
Harris et al., *J. Virol* 36, 659–664 (1980).
Helene et al., *Biochimie* 67, 777–783 (1985).
Holt et al., *Molecular & Cell Biology* 8(2), 963–973 (Feb. '88).
Inoue et a., *Nucleic Acids Res.* 15, 6131–6149 (1987).
Inoue et al., *FEBS Lett.* 215(2), 327–330 (1987).
Inoue et al., *Nucleic Acids Res.* 16, 165–168 (1985).
James, *Antiviral Chemistry & Chemotherapy,* vol. 2 #4, pp. 191–214 (1991).
Kastner et al., *The EMBO Journal* 9(5), 1603–1614 (1990).
Kawasaki et al., "Synthesis and Biophysical Studies of 2'–dRIBO–2'–F Modified Oligonucleotides," Scientific Conference in Florida, U.S.A. in Jan., 1991.
Kawasaki et al., *J. Med. Chem.* 36, 831–841 (1993).
Kibler–Herzog et al., *Nucleic Acids Res.* 19, 2979–2986 (1991).
Leiter et al., *Proc. Natl. Acad. Sci USA* 87, 3430–3434 (1990).
Marshall et al., *Science* 259, 1564–1570 (1993).
Miller and Ts'O, *Annual Reports of Medicinal Chemistry* 23, 295–304 (1988).
Miller and Ts'O, *Anti–Cancer Drug Design* 2, 117–128 (1987).
Monia et al., *J. Biol Chem.* 268(19), 14514–14522 (1993).
*Oligodeoxynucleotides: Antisense Inhibitors of Gene Expression* (J.S. Cohen, ed., CRC Press, Boca Raton, 1989).
Paterson et al., *Proc. Natl. Acad. Sci. USA* 74, 4370–4374 (1987).
Petersen and Neilsen, *Tetrahedron Letters* 31, 911–914 (1990).
Quartin et al., *Biochemistry* 28, 1040–1047 (1989).
Quartin et al., *Nucleic Acids Res.* 17(18), 7253–7262 (1989).
Rice et al., *Science* 229, 726–733 (1985).
Richards et al., *Virol.* 89, 395–408 (1978).
Robertson et al, *J. Virol,* 54, 651–660 (1985).
Saison–Behmoaras et al., *EMBO Journal* 10, 1111–1118 (1991).
Sarin et al., *Proc. Natl. Acad. Sci USA* 85, 7448–7451 (1988).
Shibabara et al., *Nuc. Acids. Res.,* vol. 17, No. 1, pp. 239–252 (1989).
Shibabara et al., *Nucleic Acids Research* 15 (11), 4403–4415 (1987).
Sitruk–Ware et al., *Contraception* 41(3), 221–243 (1990).
Stahl and Prusiner, *FASEB J.* 5, 2799–2807 (1991).
Stein et al., *Science* 261, 1004–1012 (1993).
Storey et al., *Nucleic Acids Res.* 19, 4109–4114 (1991).
Tidd et al., *Anticancer Res.* 10, 1169–1182 (1990).
Tidd et al., *British J. of Cancer* 60, 343–350 (1989).
Tseng et al., *Cancer Gene Therapy* 1(1), 65–71 (1994).
Uhlman et al., *Chemical Reviews* 90(4), 543–584 (1990).
Uhlman et al., *Chemical Reviews* 90(4), 543–584 (1990).
Verspieren et al., *Gene* 61, 307–315 (1987).
Weiss, *Science News* 139, 108–109, Feb. 16, 1991.
Westermann et al., *Biomed. Biochem. Acta* 48, 85–93 (1984).
Wickstrom et al., *The FASEB Journal* 5(5), A1443 (1991).
Wickstrom, *J. Biochem. Biophys. Meth.* 13, 97–102 (1986).
Wickstrom, *Tibetch* 10, 281–287 (1992).
Zamecnik and Stephenson, *Proc. Natl. Acad. Sci USA* 75, 280–284 (1978).
Zhang et al., *Biochemical Pharmacology* 50, 545–556 (1995).
Zurita et al., *Proc. Natl. Acad. Sci USA* 84, 2340–2344 (1987).

Fig. 2(cont.)

| | SEQ ID NO | OLIGO | DUPLEX |
|---|---|---|---|
| RNA 3' UACAGCUGUGGGUUAAGACUUUUACCUAUUUG 5'<br>5' ACACCCAAUUCUGAAAAUGG 3' | 8<br>1 | A | 1 |
| RNA 3' UACAGCUGUGGGUUAAGACUUUUACCUAUUUG 5'<br>5' ACACCCAAUUCUGAAAAUGG 3' | 8<br>6 | F | 2 |
| RNA 3' UACAGCUGUGGGUUAAGACUUUUACCUAUUUG 5'<br>5' ACACCCAAUUCUGAAAAUGG 3' | 8<br>3 | C | 3 |
| RNA 3' UACAGCUGUGGGUUAAGACUUUUACCUAUUUG 5'<br>5' ACACCCAAUUCUGAAAAUGG 3' | 8<br>2 | B | 4 |
| RNA 3' UACAGCUGUGGGUUAAGACUUUUACCUAUUUG 5'<br>5' ACACCCAAUUCUGAAAAUGG 3' | 8<br>5 | E | 5 |
| RNA 3' UACAGCUGUGGGUUAAGACUUUUACCUAUUUG 5'<br>5' ACAGACUUACCUCAGAUAAU 3' | 8<br>7 | Mis-matched | 6 |
| RNA 3' UACAGCUGUGGGUUAAGACUUUUACCUAUUUG 5' | 8 | — | — |

☐ = 2'-OCH₃, -RIBO UNITS

```
                        SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:1:

ACACCCAATT CTGAAAATGG                                                   20

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:2:

ACACCCAATT CUGAAAAUGG                                                   20

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear
```

(ii) MOLECULE TYPE: other nucleic acid (iii) HYPOTHETICAL: NO (iv) ANTI-SENSE: YES (xi) SEQUENCE DESCRIPTION: SEQ ID NO:3:

ACACCCAATT CTGAAAAUGG                                                    20

(2) INFORMATION FOR SEQ ID NO:4:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:4:

ACACCCAATT CUGAAAAUGG                                                    20

(2) INFORMATION FOR SEQ ID NO:5:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:5:

ACACCCAAUT CTGAAAATGG                                                    20

(2) INFORMATION FOR SEQ ID NO:6:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:6:

ACACCCAAUU CUGAAAAUGG                                                    20

(2) INFORMATION FOR SEQ ID NO:7:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO -continued

```
    (iv) ANTI-SENSE: YES (xi) SEQUENCE DESCRIPTION: SEQ ID NO:7:

ACAGACTTAC CTCAGATAAT                                                    20

(2) INFORMATION FOR SEQ ID NO:8:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:8:

UACAGCUGUG GGUUAAGACU UUUACCUAUU UG                                      32
```

HYBRID OLIGONUCLEOTIDE PHOSPHOROTHIOATES

This application is a continuation of Ser. No. 07/918,238 filed Jul. 23, 1992, U.S. Pat. No. 5,275,201.

BACKGROUND OF THE INVENTION

1. Field of the Invention

The invention relates to synthetic oligonucleotides that are useful for studies of gene expression and in the antisense oligonucleotide therapeutic approach. More particularly, the invention relates to synthetic oligonucleotides that have improved qualities for such applications resulting from modifications in the sugar phosphate backbone of the oligonucleotides.

2. Summary of the Related Art

The potential for the development of an antisense oligonucleotide therapeutic approach was first suggested in three articles published in 1977 and 1978. Paterson et al., Proc. Natl. Acad. Sci. USA 74: 4370–4374 (1977) discloses that cell-free translation of mRNA can be inhibited by the binding of an oligonucleotide complementary to the mRNA. Zamecnik and Stephenson, Proc. Natl. Acad. Sci. USA 75: 280–284 and 285–288 (1978) discloses that a 13-mer synthetic oligonucleotide that is complementary to a part of the Rous sarcoma virus (RSV) genome inhibits RSV replication in infected chicken fibroblasts and inhibits RSV-mediated transformation of primary chick fibroblasts into malignant sarcoma cells.

These early indications that synthetic oligonucleotides can be used to inhibit virus propagation and neoplasia have been followed by the use of synthetic oligonucleotides to inhibit a wide variety of viruses. Goodchild et al., U.S. Pat. No. 4,806,463 (the teachings of which are hereby incorporated by reference) discloses inhibition of human immunodeficiency virus (HIV) by synthetic oligodeoxynucleotides complementary to various regions of the HIV genome. Leiter et al., Proc. Natl. Acad. Sci. USA 87: 3430–3434 (1990) discloses inhibition of influenza virus by synthetic oligonucleotides. Agris et al., Biochemistry 25: 6268–6275 (1986) discloses the use of synthetic oligonucleotides to inhibit vesicular stomatitis virus (VSV). Gao et al. Antimicrob. Agents Chem. 34: 808–812 (1990) discloses inhibition of herpes simplex virus by synthetic oligonucleotides. Birg et al., Nucleic Acids Res. 18: 2901–2908 (1990) discloses inhibition of simian virus (SV40) by synthetic oligonucleotides. Storey et al., Nucleic Acids Res. 19: 4109–4114 (1991) discloses inhibition of human papilloma virus (HPV) by synthetic oligonucleotides. The use of synthetic oligonucleotides and their analogs as antiviral agents has recently been extensively reviewed by Agrawal, Trends in Biotech 10: 152–158 (1992).

In addition, synthetic oligonucleotides have been used to inhibit a variety of non-viral pathogens, as well as to selectively inhibit the expression of certain cellular genes. Thus, the utility of synthetic oligonucleotides as agents to inhibit virus propagation, propagation of non-viral pathogens and selective expression of cellular genes has been well established. However, there is a need for improved oligonucleotides that have greater efficacy in inhibiting such viruses, pathogens and selective gene expression. Various investigators have attempted to meet this need by preparing and testing oligonucleotides having modifications in their internucleotide linkages. Several investigations have shown that such modified oligonucleotides are more effective than their unmodified counterparts. Sarin et al., Proc. Natl. Acad. Sci. USA 85: 7448–7451 (1988) teaches that oligodeoxynucleoside methylphosphonates are more active as inhibitors of HIV-1 than conventional oligodeoxynucleotides. Agrawal et al., Proc. Natl. Acad. Sci. USA 85: 7079–7083 (1988) teaches that oligonucleotide phosphorothioates and certain oligonucleotide phosphoramidates are more effective at inhibiting HIV-1 than conventional oligodeoxynucleotides. Agrawal et al., Proc. Natl. Acad. Sci. USA 86. 7790–7794 (1989) discloses the advantage of oligonucleotide phosphorothioates in inhibiting HIV-1 in early and chronically infected cells.

In addition, chimeric oligonucleotides having more than one type of internucleoside linkage within the oligonucleotide have been developed. Chimeric oligonucleotides contain deoxyribonucleosides only, but have regions containing different internucleoside linkages. Pederson et al., U.S. Pat. No. 5,149,797, the teachings of which are hereby incorporated by reference, discloses chimeric oligonucleotides having an oligonucleotide phosphodiester or oligonucleotide phosphorothioate core sequence flanked by oligonucleotide, methylphosphonates or phosphoramidates. Furdon et al., Nucleic Acids Res. 17: 9193–9204 (1989) discloses chimeric oligonucleotides having regions of oligonucleotide phosphodiesters in addition to either oligonucleotide phosphorothioate or methylphosphonate regions. Quartin et al., Nucleic Acids Res. 17: 7523–7562 (1989) discloses chimeric oligonucleotides having regions of oligonucleotide phosphodiesters and oligonucleotide methylphosphonates. Each of the above compounds contains deoxyribonucleotide phosphorothioates which have reduced duplex stability. Atabekov et al., FEBS Letters 232: 96–98 (1988) discloses chimeric oligonucleotides in which all internucleoside linkages are phosphodiester linkages, but in which regions of ribonucleotides and deoxyribonucleotides are mixed. Inoue et al., FEBS Letters, 215: 237–250 (1987) discloses chimeric oligonucleotides having only phosphodiester linkages, and regions of deoxyribonucleotides and 2'-OMe-ribonucleotides. None of these compounds having solely phosphodiester linkages exhibit either endonuclease or exonuclease resistance.

Many of these modified oligonucleotides have contributed to improving the potential efficacy of the antisense oligonucleotide therapeutic approach. However, certain deficiencies remain in the known oligonucleotides, and these deficiencies can limit the effectiveness of such oligonucleotides as therapeutic agents. Wickstrom, J. Biochem. Biophys. Methods 13: 97–102 (1986) teaches that oligonucleotide phosphodiesters are susceptible to nuclease-mediated degradation. Such nuclease susceptibility can limit the bioavailability of oligonucleotides in vivo. Agrawal et al., Proc. Natl. Acad. Sci. USA 87: 1401–1405 (1990) teaches that oligonucleotide phosphoramidates or methylphosphonates when hybridized to RNA do not activate RNase H, the activation of which can be important to the function of antisense oligonucleotides. Agrawal et al., Nucleosides & Nucleotides 8: 5–6 (1989) teaches that oligodeoxyribonucleotide phosphorothioates have reduced duplex stability when hybridized to RNA.

There is, therefore, a need for improved oligonucleotides that overcome the deficiencies of oligonucleotides that are known in the art. Ideally, such oligonucleotides should be resistant to nucleolytic degradation, should form stable duplexes with RNA, and should activate RNase H when hybridized with RNA.

BRIEF SUMMARY OF THE INVENTION

The invention provides hybrid oligonucleotides (containing segments of deoxy- and ribo nucleotides) that resist nucleolytic degradation, form stable duplexes with RNA or DNA, and activate RNase H when hybridized with RNA. Oligonucleotides according to the invention provide these features by having phosphorothioate and/or phosphorodithioate internucleoside linkages and segments of oligodeoxyribonucleotides as well as segments of either oligoribonucleotides or 2'-substituted-oligoribonucleotides. For purposes of the invention, the term "2'-substituted" means substitution of the 2'-OH of the ribose molecule with, -O-lower alkyl containing 1–6 carbon atoms, aryl or substituted aryl or allyl having 2–6 carbon atoms e.g. 2'-OMe, 2'-O-allyl, 2'-Oaryl, 2'-O-alkyl, 2'-halo, or 2'-amino, but not with 2'-H, wherein allyl, aryl, or alkyl groups may be unsubstituted or substituted, e.g., with halo, hydroxy, trifluoromethyl, cyano, nitro, acyl, acyloxy, alkoxy, carboxyl, carbalkoxyl or amino groups.

An object of the invention is to provide oligonucleotides that can be used to analyze and explain the importance to the effectiveness of antisense oligonucleotides of the parameters of nuclease resistance, duplex stability and RNase H activation. Another object of the invention is to provide oligonucleotides that are effective for regulating cellular, pathogen, or viral gene expression at the mRNA level. Yet another object of the invention is to provide therapeutic oligonucleotides that have great efficacy in the antisense oligonucleotide therapeutic approach. Oligonucleotides according to the invention are useful in satisfying each of these objects of the invention.

BRIEF DESCRIPTION OF THE DRAWINGS

In FIG. 1A, profiles A, B and C are of oligonucleotides F (SEQ ID NO: 6), C (SEQ ID NO: 3) and A (SEQ ID NO: 1), respectively after 420 minutes SVPD digestion. In FIG. 1B, profile A is of an undigested oligonucleotide phosphodiester and profile B is of the same after 1 minute SVPD digestion (SVPD concentration one tenth that in Panel A).

DETAILED DESCRIPTION OF THE PREFERRED EMBODIMENTS

Figure 1A:
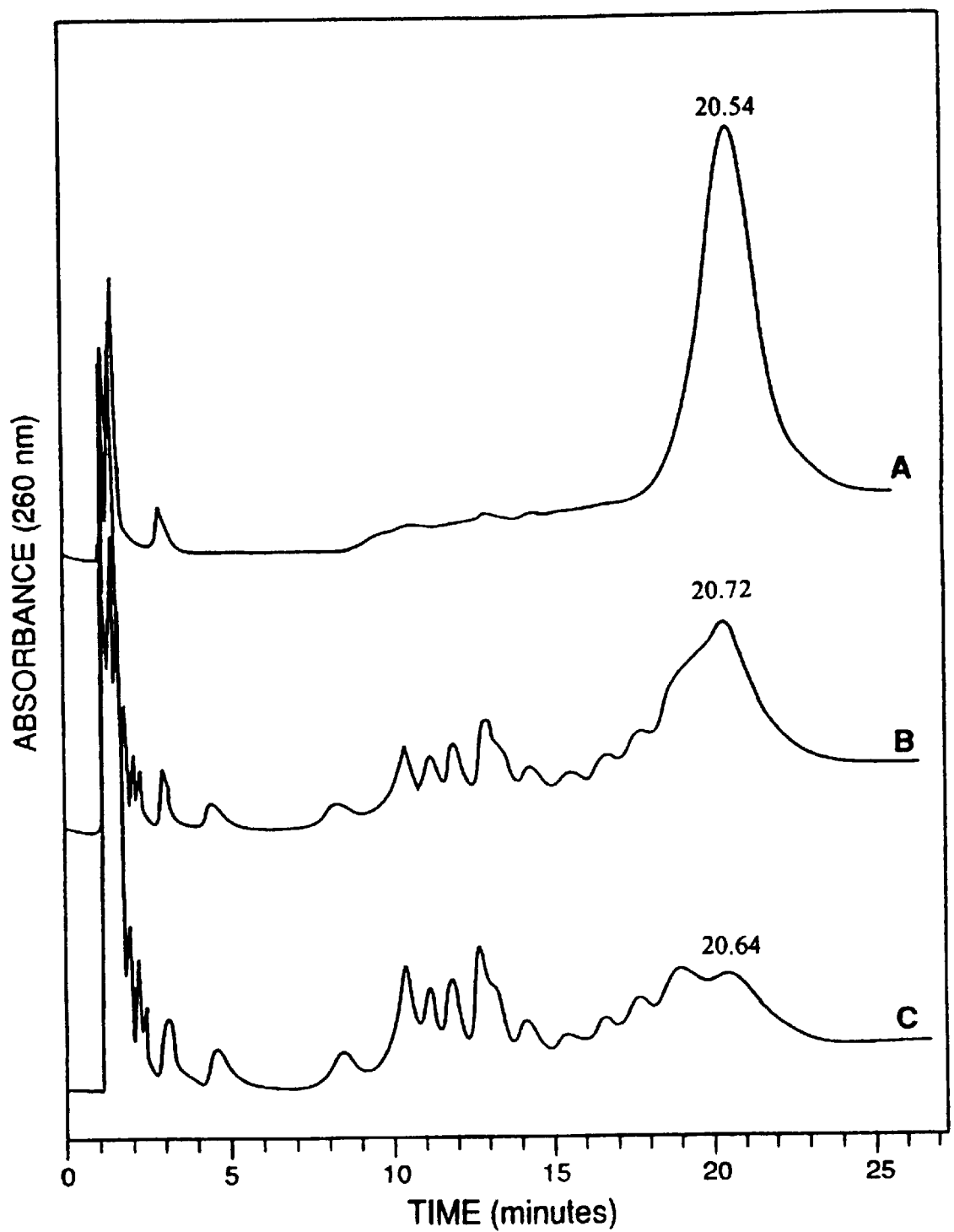
FIGS. 1A–1B shows ion exchange HPLC analysis of nuclease treated oligonucleotides.

In a first aspect, the invention provides oligonucleotides that are useful for studying the parameters that are important for effective antisense oligonucleotide action. For purposes of the invention, the term oligonucleotide includes polymers of two or more ribonucleotides, deoxyribonucleotides or both, with ribonucleotide and/or deoxyribonucleotide monomers being connected together via 5' to 3' linkages which may include any of the linkages that are known in the antisense oligonucleotide art. In addition, the term oligonucleotides includes such molecules having modified nucleic acid/bases and/or sugars, as well as such molecules having added substituents, such as diamines, cholesteryl or other lipophilic groups. Certain preferred combinations of monomers and inter-monomer linkages are discussed in greater detail below.

It is generally believed that the activity of an antisense oligonucleotide depends on the binding of the oligonucleotide to the target nucleic acid, thus disrupting the function of the target, either by hybridization arrest or by destruction of target RNA by RNase H. These mechanisms of action suggest that two parameters should be important to antisense oligonucleotide activity: duplex stability and RNase H activation. Duplex stability is important, since the oligonucleotide presumably must form a duplex (or triplex in the Hoogsteen pairing mechanism) with the target nucleic acid to act either by hybridization arrest or by RNase H-mediated target destruction. RNase H activation (the ability to activate RNase H when hybridized with target RNA) is implicated when the target nucleic acid is RNA, since such activation can lead to the effective destruction of the target RNA molecule. In addition, for an antisense oligonucleotide to act in vivo, it must survive long enough to interact with the target nucleic acid. Given the fact that the in vivo environment contains endonuclease and exonuclease activities, a third parameter arises from this requirement; namely that the antisense oligonucleotide should resist nucleolytic degradation.

To analyze and explain the importance of each of these parameters to the effectiveness of antisense oligonucleotides, it is necessary to have oligonucleotides that vary in each of these parameters. The properties of several known oligonucleotides are shown in Table I, below.

TABLE I

PROPERTIES OF OLIGONUCLEOTIDES

| Oligonucleotide | Duplex Stability[1] | Nuclease Resistance[2] | RNase H Activation[3] |
|---|---|---|---|
| Oligodeoxyribonucleotide (phosphate) | — | — | Yes |
| Oligodeoxyribonucleotide (phosphorothioate) | Lower | + | Yes |
| Oligodeoxyribonucleotide (phosphorodithioate) | Lower | ++ | Yes |
| Oligodeoxyribonucleotide (selenoate) | Lower | + | N.K. |
| Oligodeoxyribonucleotide (phosphoramidate) | Lower | +++ | No |
| Oligoribonucleotide (phosphate) | Higher | — | No |
| Oligoribonucleotide (phosphorothioate) | Higher | + | No |
| 2'-OMe-Oligonucleotide (phosphate) | Higher | + | No |
| 2'-OMe-Oligoribonucleotide (phosphorothioate) | Higher | ++ | No |
| Oligodeoxyribonucleotide (methylphosphonate) | Lower | +++ | No |

[1]Duplex stability of oligonucleotide to complementary oligoribonucleotide under physiological conditions, compared to DNA-RNA stability.
[2]Compared to DNA (phosphodiesterase digestion).
[3]Activation of RNase H by the duplex formed between oligonucleotide and RNA.
N.K. - Not known Hybrid oligonucleotides according to the invention form more stable duplexes with complementary RNA than oligodeoxyribonucleotide phosphorothioates. In addition, they are more resistant to endonucleolytic and exonucleolytic degradation than oligodeoxyribonucleotide phosphorothioates and they normally activate RNase H. Consequently, oligonucleotides according to the invention complement the oligonucleotides shown in Table I in studies of the parameters involved in the effectiveness of antisense oligonucleotides.

With respect to this first aspect of the invention, oligonucleotides according to the invention can have any oligonucleotide sequence, since complementary oligonucleotides used in such study can be prepared having any oligonucleotide sequence. Oligonucleotides according to this aspect of the invention are characterized only by the following features. First, at least some of the internucleoside linkages present in oligonucleotides according to the invention are phosphorothioate and/or phosphorodithioate linkages. In various embodiments, the number of phosphorothioate and/or phosphorodithioate internucleotide linkages can range from 1 to as many internucleotide linkages as are present in the oligonucleotide. Thus, for purposes of the invention, the term oligonucleotide phosphorothioate and/or phosphorodithioate is intended to encompass every such embodiment. In a preferred embodiment, oligonucleotides according to the invention will range from about 2 to about 50 nucleotides in length, and most preferably from about 6 to about 50 nucleotides in length. Thus, in this preferred embodiment, oligonucleotides according to the invention will have from 1 to about 49 phosphorothioate and/or phosphorodithioate internucleotide linkages.

A second feature of oligonucleotides according to this aspect of the invention is the presence of deoxyribonucleotides. Oligonucleotides according to the invention contain at least one deoxyribonucleotide. Preferably oligonucleotides according to the invention contain four or more deoxyribonucleotides in a contiguous block, so as to provide an activating segment for RNase H. In certain preferred embodiments, more than one such activating segment will be present. Such segments may be present at any location within the oligonucleotide. There may be a majority of deoxyribonucleotides in oligonucleotides according to the invention. In fact, such oligonucleotides may have as many as all but one nucleotide being deoxyribonucleotides. Thus, in a preferred embodiment, having from about 2 to about 50 nucleotides or most preferably from about 6 to about 50 nucleotides, the number of deoxyribonucleotides present will range from 1 to about 49 deoxyribonucleotides.

A third feature of oligonucleotides according to this aspect of the invention is the presence of ribonucleotides, 2'-substituted ribonucleotides or combinations thereof. For purposes of the invention, the term "2'-substituted" means substitution of the 2'-OH of the ribose molecule with, e.g., 2'-OMe, 2'-O-allyl, 2'-O-aryl, 2'-O-alkyl, 2'-halo, or 2'-amino, but not with 2'-H, wherein allyl, aryl, or alkyl groups may be unsubstituted or substituted, e.g., with halo, hydroxy, trifluoromethyl, cyano, nitro, acyl, acyloxy, alkoxy, carboxyl, carbalkoxyl or amino groups. Oligonucleotides according to the invention contain at least one ribonucleotide and/or 2'-substituted ribonucleotide. In a preferred embodiment, such oligonucleotides have 6 or more ribonucleotides and/or 2'-substituted ribonucleotides to enhance duplex stability. Such ribonucleotides and/or 2'-substituted ribonucleotides can be present singly, in pairs, or in larger contiguous segments, and may be present at any position within the oligonucleotide or at multiple positions within the oligonucleotide. Such ribonucleotides and/or 2'-substituted ribonucleotides may comprise as many as all but one nucleoside within the oligonucleotides. Thus, in a preferred embodiment, having from about 2 to about 50 nucleotides or most preferably from about 6 to about 50 nucleotides, the number of ribonucleosides or 2'-substituted ribonucleotides will range from about 1 to about 49 deoxyribonucleotides.

The ability to vary the numbers and positions of phosphorothioate and/or phosphorodithioate internucleotide linkages, deoxyribonucleotides, and ribonucleotides or 2'-substituted ribonucleotides allows the investigator to examine in detail how each of these variables affects the parameters of nuclease resistance, duplex stability and RNase H activation. The ability to vary the size of the oligonucleotide allows examination of yet another parameter. In addition, smaller oligos (e.g., dimers) can be used as building blocks for larger oligos. Thus, the embodiments described above are useful in such studies.

In a second aspect, the invention provides hybrid oligonucleotides that are effective in inhibiting viruses, pathogenic organisms, or the expression of cellular genes. The ability to inhibit such agents is clearly important to the treatment of a variety of disease states. Oligonucleotides according to this aspect of the invention share the characteristics of the above-described oligonucleotides, except that the oligonucleotide sequence of oligonucleotides according to this aspect of the invention is complementary to a nucleic acid sequence that is from a virus, a pathogenic organism or a cellular gene. Preferably such oligonucleotides are from about 6 to about 50 nucleotides in length. For purposes of the invention, the term "oligonucleotide sequence that is complementary to a nucleic acid sequence" is intended to mean an oligonucleotide sequence (2 to about 50 nucleotides) that binds to the nucleic acid sequence under physiological conditions, e.g. by Watson-Crick base pairing (interaction between oligonucleotide and single-stranded nucleic acid) or by Hoogsteen base pairing (interaction between oligonucleotide and double-stranded nucleic acid) or by any other means including in the case of a oligonucleotide binding to RNA, pseudoknot formation. Such binding (by Watson Crick base pairing) under physiological conditions is measured as a practical matter by observing interference with the function of the nucleic acid sequence.

The nucleic acid sequence to which an oligonucleotide according to the invention is complementary will vary, depending upon the agent to be inhibited. In many cases the nucleic acid sequence will be a virus nucleic acid sequence. The use of antisense oligonucleotides to inhibit various viruses is well known, and has recently been reviewed in Agrawal, Trends in Biotech 10:152–158 (1992). Viral nucleic acid sequences that are complementary to effective antisense oligonucleotides have been described for many viruses, including human immunodeficiency virus type I (U.S. Pat. No. 4,806,463, the teachings of which are hereby incorporated by reference), herpes simplex virus (U.S. Pat. No. 4,689,320, the teachings of which are hereby incorporated by reference), influenza virus (U.S. Pat. No. 5,194,428; the teachings of which are hereby incorporated by reference), and Human papilloma virus (Storey et al., Nucleic Acids Res. 19:4109–4114 (1991)). Sequences complementary to any of these nucleic acid sequences can be used for oligonucleotides according to the invention, as can be oligonucleotide sequences complementary to nucleic acid sequences from any other virus. Additional viruses that have known nucleic acid sequences against which antisense oligonucleotides can be prepared include foot and mouth disease virus (See Robertson et al., J. Virology 54: 651 (1985); Harris et al., J. Virology 36: 659 (1980)), yellow fever virus (See Rice et al., Science 229: 726 (1985)), varicella-zoster virus (See Davison and Scott, J. Gen. Virology 67: 2279 (1986), and cucumber mosaic virus (See Richards et al., Virology 89: 395 (1978)).

Alternatively, oligonucleotides according to the invention can have an oligonucleotide sequence complementary to a nucleic acid sequence of a pathogenic organism. The nucleic acid sequences of many pathogenic organisms have been described, including the malaria organism, *Plasmodium falciparum*, and many pathogenic bacteria. Oligonucleotide sequences complementary to nucleic acid sequences from any such pathogenic organism can be used in oligonucleotides according to the invention. Examples of pathogenic eukaryotes having known nucleic acid sequences against which antisense oligonucleotides can be prepared include *Trypanosom abrucei gambiense* and *Leish mania* (See Campbell et al., Nature 311: 350 (1984)), *Fasciola hepatica* (See Zurita et al., Proc. Natl. Acad. Sci. USA 84: 2340 (1987). Antifungal oligonucleotides can be prepared using a target hybridizing region having an oligonucleotide sequence that is complementary to a nucleic acid sequence from, e.g., the chitin synthetase gene, and antibacterial oligonucleotides can be prepared using, e.g., the alanine racemase gene.

In yet another embodiment, the oligonucleotides according to the invention can have an oligonucleotide sequence complementary to a cellular gene or gene transcript, the abnormal expression or product of which results in a disease state. The nucleic acid sequences of several such cellular genes have been described, including prion protein (Stahl and Prusiner, FASEB J. 5: 2799–2807 (1991)), the amyloid-like protein associated with Alzheimer's disease (U.S. Pat. No. 5,015,570, the teachings of which are hereby incorporated by reference), and various wellknown oncogenes and proto-oncogenes, such as c-myb, c-myc, c-abl and n-ras. In addition, oligonucleotides that inhibit the synthesis of structural proteins or enzymes involved largely or exclusively in spermatogenesis, sperm motility, the binding of the sperm to the egg or any other step affecting sperm viability may be used as contraceptives. Similarly, contraceptives for women may be oligonucleotides that inhibit proteins or enzymes involved in ovulation, fertilization, implantation or in the biosynthesis of hormones involved in those processes.

Hypertension may be controlled by oligodeoxynucleotides that suppress the synthesis of angiotensin converting enzyme or related enzymes in the renin/angiotensin system; platelet aggregation may be controlled by suppression of the synthesis of enzymes necessary for the synthesis of thromboxane A2 for use in myocardial and cerebral circulatory disorders, infarcts, arteriosclerosis, embolism and thrombosis; deposition of cholesterol in arterial wall may be inhibited by suppression of the synthesis of fatty acid co-enzyme A: cholesterol acyl transferase in arteriosclerosis; inhibition of the synthesis of cholinephosphotransferase may be useful in hypolipidemia.

There are numerous neural disorders in which hybridization arrest may be used to reduce or eliminate adverse effects of the disorder. For example, suppression of the synthesis of monoamine oxidase may be used in Parkinson's disease; suppression of catechol o-methyl transferase may be used to treat depression; and suppression of indole N-methyl transferase may be used in treating schizophrenia.

Suppression of selected enzymes in the arachidonic acid cascade which leads to prostaglandins and leukotrienes may be useful in the control of platelet aggregation, allergy, inflammation, pain and asthma.

Suppression of the protein expressed by the multidrug resistance (mdr) gene, which can be responsible for development of resistance of tumors to a variety of anti-cancer drugs and is a major impediment in chemotherapy may prove to be beneficial in the treatment of cancer. Oligonucleotide sequences complementary to nucleic acid sequences from any of these genes can be used for oligonucleotides according to the invention, as can be oligonucleotide sequences complementary to any other cellular gene or gene transcript, the abnormal expression or product of which results in a disease state.

Antisense regulation of gene expression in plant cells has been described in U.S. Pat. No. 5,107,065, the teachings of which are hereby incorporated by reference.

In a third aspect, the invention provides therapeutic pharmaceutical formulations of oligonucleotides that are effective for treating virus infection, infections by pathogenic organisms, or disease resulting from abnormal gene expression or from the expression of an abnormal gene product. Such therapeutic pharmaceutical formulations comprise the oligonucleotides according to the second aspect of the invention in a pharmaceutically acceptable carrier.

In a fourth aspect, the invention provides a method for inhibiting the gene expression of a virus, a pathogenic organism or a cellular gene, the method comprising the step of providing oligonucleotides according to the invention to cells infected with the virus or pathogenic organism in the former two cases or to cells generally in the latter case. Such methods are useful in studying gene expression and the function of specific genes.

In a fifth aspect, the invention provides a method of treating a diseased human or animal in which the disease results from infection with a virus or pathogenic organism, or from the abnormal expression or product of a cellular gene. The method comprises administering therapeutic pharmaceutical formulations of oligonucleotides according to the invention to the diseased human or animal. Preferably, the routes of such administration will include oral, intranasal, rectal and topical administration. In such methods of treatment according to the invention the oligonucleotides may be administered in conjunction with other therapeutic agents, e.g., AZT in the case of AIDS.

A variety of viral diseases may be treated by the method of treatment according to the invention, including AIDS, ARC, oral or genital herpes, papilloma warts, flu, foot and mouth disease, yellow fever, chicken pox, shingles, adult T cell-leukemia, and hepatitis. Among fungal diseases that may be treatable by the method of treatment according to the invention are candidiasis, histoplasmosis, cryptococcocis, blastomycosis, aspergillosis, sporotrichosis, chromomycosis, dermatophytosis and coccidioidomycosis. The method might also be used to treat rickettsial diseases (e.g., typhus, Rocky Mountain spotted fever), as well as sexually transmitted diseases caused by *Chlamydia trachomatis* or *Lymphogranuloma venereum*. A variety of parasitic diseases may be treated by the method according to the invention, including amebiasis, Chegas' disease, toxoplasmosis, pneumocystosis, giardiasis, cryptosporidiosis, trichomoniasis, and *Pneumocystis carini* pneumonia; also worm (helminthic) diseases such as ascariasis, filariasis, trichinosis, schistosomiasis and nematode or cestode infections. Malaria may be treated by the method of treatment of the invention regardless of whether it is caused by *P. falcip arum, P. vivax, P. orale,* or *P. malariae*.

The infectious diseases identified above may all be treated by the method of treatment according to the invention because the infectious agents for these diseases are known and thus oligonucleotides according to the invention can be prepared, having oligonucleotide sequence that is complementary to a nucleic acid sequence that is an essential nucleic acid sequence for the propagation of the infectious agent, such as an essential gene.

Other disease states or conditions that may be treatable by the method according to the invention are those which result from an abnormal expression or product of a cellular gene. These conditions may be treated by administration of oligonucleotides according to the invention., and have been discussed earlier in this disclosure.

Oligonucleotides according to the invention can be synthesized by procedures that are well known in the art. Alternatively, and preferably such oligonucleotides can be synthesized by the H-phosphonate approach described in U.S. Pat. No. 5,149,798, the teachings of which are hereby incorporated by reference, and in Agrawal and Tang, Tetrahedron Lett. 31: 7541–7544 (1990). Oligonucleotides according to the invention can be made even more resistant to nucleolytic degradation through the addition of cap structures at the 5' and/or 3' end.

The following examples are intended to further illustrate certain preferred embodiments of the invention and are not intended to be limiting in nature.

EXAMPLE 1

Synthesis of Hybrid Oligonucleotide Phosphorothioates

Hybrid oligonucleotide phosphorothioates were synthesized on CPG on a 5–6 µmole scale on an automated synthesizer (model 8700, Millipore, Milford, Mass.) using the H-phosphonate approach described in U.S. Pat. No. 5,149,798. Deoxynucleoside H-phosphonates were obtained from Millipore. 2'-OMe ribonucleotide H-phosphonates were synthesized by standard procedures. Segments of oligonucleotides containing 2'-OMe nucleoside were assembled by using 2'-OMe ribonucleoside H-phosphonates for the desired cycles. Similarly, segments of oligonucleotides containing deoxyribonucleosides were assembled by using deoxynucleoside H-phosphonates for the desired cycles. After assembly, CPG bound oligonucleotide H-phosphonate was oxidized with sulfur to generate the phosphorothioate linkage. Oligonucleotides were then deprotected in concentrated $NH_4OH$ at 40° C. for 48 hours.

Crude oligonucleotide (about 500 $A_{260}$ units) was analyzed on reverse low pressure chromatography on a $C_{18}$ reversed phase medium. The DMT group was removed by treatment with 80% aqueous acetic acid, then the oligonucleotides were dialyzed against distilled water and lyophilized.

The oligonucleotides synthesized are shown in Table II, below.

Figure 1B:
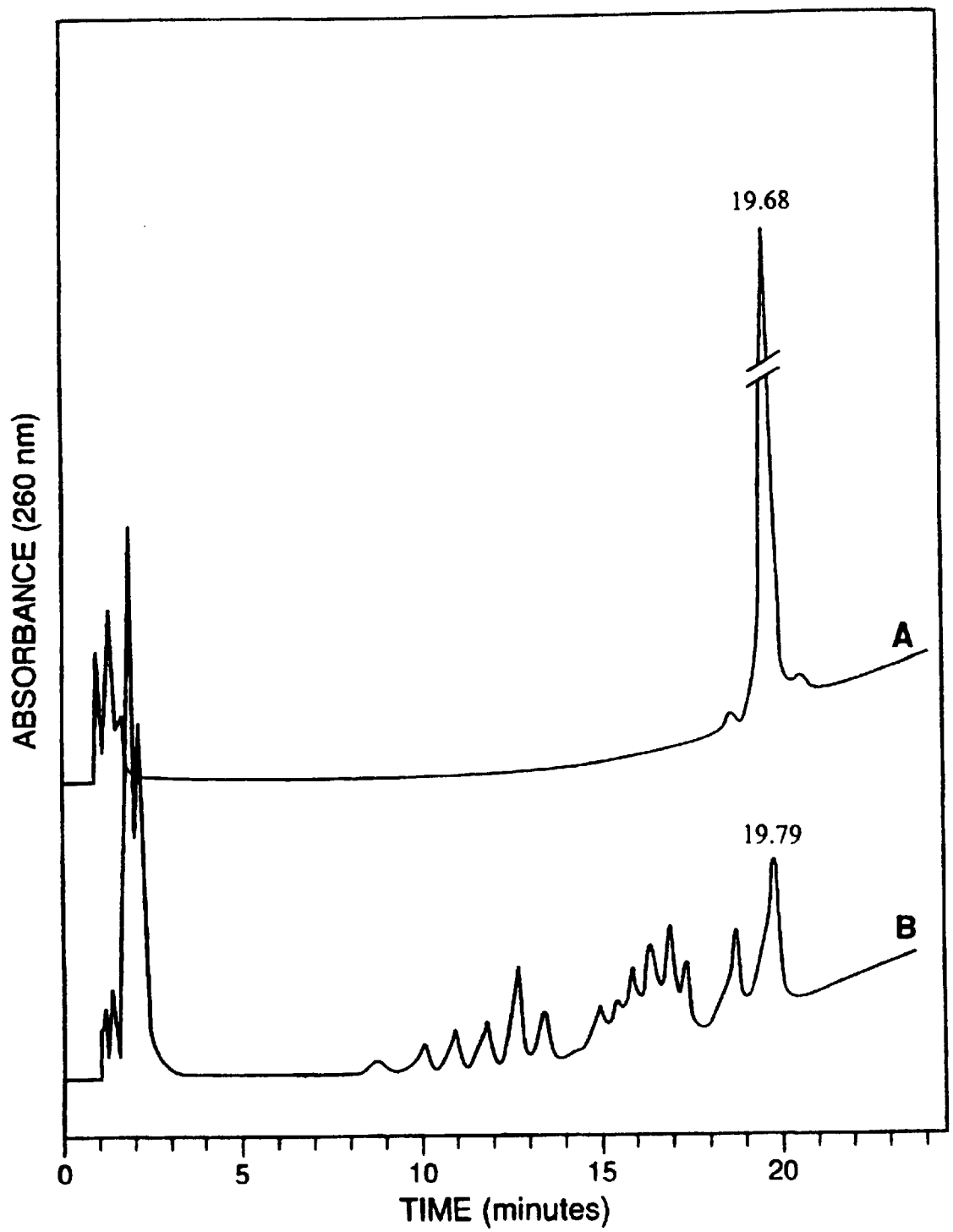

ID NO: 3) and F (SEQ ID NO: 6) were dissolved in 500 µl buffer (40 mM $NH_4CO_3$, pH 0.4+20 mM $MgCl_2$) and mixed with 0.1 units SVPD. The mixture was incubated at 37° C. for 420 minutes. After 0, 200 and 420 minutes, 165 µl aliquots were removed and analyzed using ion exchange HPLC. The results are shown in FIG. 1. Oligonucleotide F was very resistant to phosphodiesterase, whereas oligonucleotide A (SEQ ID NO: 1) was digested almost to completion and oligonucleotide A (SEQ ID NO: 3) was digested to 50% (panel A). An oligonucleotide phosphodiester was digested to about 80% in one minute using one tenth of the concentration of SVPD. (panel B)

These results indicate that the presence of 2'-OMe ribonucleotides in an oligonucleotide phosphorothioate enhances resistance to exonucleolytic digestion and that this enhanced resistance increases when a larger proportion of 2'-OMe ribonucleotides are used. Due to the similar character and behavior of ribonucleotides, other 2'-substituted ribonucleotides and 2'-OMe ribonucleotides, these results also suggest that similar enhancement of nuclease resistance would be obtained for hybrid oligonucleotide phosphorothioates and/or phosphorodithioates having ribonucleotides, 2'-substituted ribonucleotides, or a mixture of ribonucleotides and 2'-substituted ribonucleotides.

EXAMPLE 3

Relative Duplex Stability of Hybrid Oligonucleotide Phosphorothloates

Oligonucleotides A (SEQ ID NO: 1)–F (SEQ ID NO: 6) were tested for the relative stability of duplexes formed between them and complementary oligodeoxyribonucleotides, and with complementary oli-

TABLE II

HYBRID OLIGONUCLEOTIDE PHOSPHOROTHIOATES* SYNTHESIZED

| Oligo | Structure |
|---|---|
| A(SEQ ID NO:1) | 5'A C A C C C A A T T C T G A A A A T G G 3' |
| B(SEQ ID NO:2) | A C A C C C A A T T C <u>U G A A A A U</u> G G |
| C(SEQ ID NO:3) | <u>A C A</u> C C C A A T T C T G A A <u>A A U</u> G G |
| D(SEQ ID NO:4) | A <u>C</u> A C C <u>C A A</u> T T C <u>U G</u> A A A A <u>U G</u> G |
| E(SEQ ID NO:5) | A <u>C A C C C A A U</u> T C T G A A A A T G G |
| F(SEQ ID NO:6) | <u>A C A C C C A A U U C U G A A A A U G</u> G |

Underlined sequences contain 2'-OMe ribonucleoside.
*All internucleoside linkages are phosphorothioate linkages for oligos A–F.

EXAMPLE 2

Relative Nuclease Resistance of Hybrid Oligonucleotide Phosphorothioates

To test the relative nuclease resistance of various hybrid oligonucleotide phosphorothioates, the oligonucleotides were treated with snake venom phosphodiesterase (SVPD). About 0.2 $A_{260}$ units of oligos A (SEQ ID NO: 1), C (SEQ goribonucleotides. In separate reactions, each oligonucleotide A–F was mixed with an equivalent quantity (0.2 $A_{260}$ units) of its complementary oligonucleotide in 150 mM NaCl, 10 mM $Na_2PO_4$, 1 mM EDTA, pH 7. The mixture was heated to 85° C. for 5 minutes, then cooled to 30° C. The temperature was then increased from 30° C. to 80° C. at a rate of 1° C. per minute and $A_{260}$ was recorded as a function of temperature. The results are shown in Table III, below.

TABLE III

MELTING TEMPERATURE OF DUPLEXES

| | DNA-DNA Duplex | | DNA-RNA Duplex | | | DNA-RNA Duplex w/Magnesium | |
|---|---|---|---|---|---|---|---|
| Oligonucleotide | Tm DNA (° C.) | Difference in Tm compared to oligonucleotide A(° C.) | Tm RNA (° C.) | Difference in Tm compared to oligonucleotide A(° C.) | Tm DNA-RNA Duplex-Tm DNA Duplex (° C.) | Tm RNA (° C.) | Difference in Tm compared to oligonucleotide A(° C.) |
| A(SEQ ID NO:1) | 51.1 | 0 | 43.4 | 0 | −7.7 | 48.1 | 0 |
| B(SEQ ID NO:2) | 48.3 | −2.8 | 50.9 | 7.5 | 2.6 | 58.4 | 10.3 |
| C(SEQ ID NO:3) | 49.9 | −1.2 | 48.9 | 5.5 | −1.0 | 54.2 | 6.1 |
| D(SEQ ID NO:4) | 45.1 | −6.0 | 50.9 | 7.5 | 5.8 | 56.1 | 8.0 |
| E(SEQ ID NO:5) | 47.2 | −3.9 | 51.1 | 7.7 | 3.9 | 56.5 | 8.4 |
| F(SEQ ID NO:6) | 47.6 | −3.5 | 61.1 | 17.7 | 13.5 | 69.1 | 21.0 |

These results reveal that when the complementary oligonucleotide is an oligoribonucleotide, the presence of 2'-OMe ribonucleotides enhances duplex stability, and that this enhancement increases with increased proportions of 2'-OMe ribonucleotides. These results should be similarly applicable to hybrid oligonucleotide phosphorothioates and/ or phosphorodithioates containing ribonucleotides, 2'-substituted ribonucleotides, or mixtures of ribonucleotides and 2'-substituted ribonucleotides. Thus, the hybrid oligonucleotide phosphorothioates and/or phosphorodithioates according to the invention should bind viral RNA or virus, pathogenic organism or cellular mRNA with greater affinity than ordinary oligodeoxynucleotide phosphorothioates.

EXAMPLE 4

Activation of RNase H by Hybrid Oligonucleotide Phosphorothioates

Oligonucleotide phosphorothioates and various hybrid oligonucleotide phosphorothioates were studied for their RNase H activation properties. Oligonucleotide A (SEQ ID NO: 1) (Table II), an oligonucleotide phosphorothioate which is known to activate RNase H, was used as a control. Oligonucleotide A (SEQ ID NO: 6) (a 2'-OMe analog of oligonucleotide phosphorothioate) and oligonucleotides C (SEQ ID NO: 3), B (SEQ ID NO: 2), and E (SEQ ID NO: 5), hybrid oligonucleotides, were studied for their ability to activate RNase H.

Figure 2:
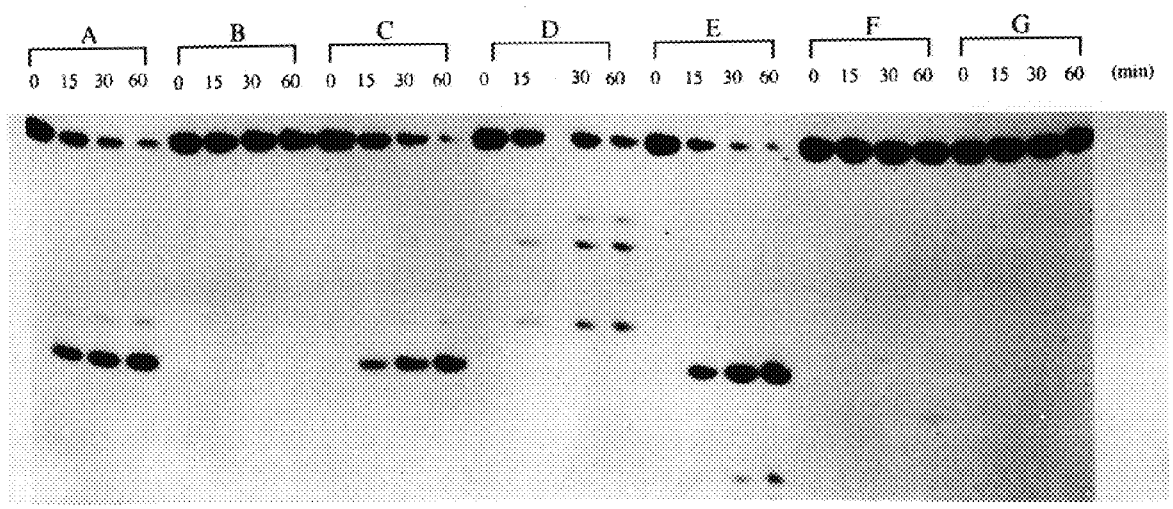
FIG. 2 shows results of RNase H activation studies for oligonucleotides, as described in Example 4.

To carry out the experiment, a complementary 32-mer oligoribonucleotide was synthesized (FIG. 2) and kinased at the 5'-end, $^{32}$P-labeled 32-mer RNA (0.003 $A_{260}$ units; 0.01 μg) and oligonucleotides (0.0635 $A_{260}$ units; 1.9 μg) were mixed in the 20 μl of buffer (0.15 M NaCl, 0.01 $MgCl_2$, 0.01 M Tris-HCl, pH 7.9, containing 0.001 M DTT. The mixture was incubated with 6 units of RNase H (*E. coli*) at 37° C. Aliquots of 4.5 μl were removed at 0, 15, 30, and 60 minutes and analyzed on polyacrylamide gel electrophoresis.

Oligonucleotide A (SEQ ID NO: 1) (duplex A in FIG. 2) showed site specific cleavage of RNA by RNase H. Oligonucleotide F (SEQ ID NO: 6) (2'-OMe analog; Duplex 2) showed no cleavage of RNA in presence of R:Nase H. Hybrid oligonucleotide C (SEQ ID NO: 3), B (SEQ ID NO: 2) and E (SEQ ID NO: 5) (Duplexes 3, 4, 5, resp.) showed site specific cleavage of RNA by RNase H. Duplex 6, in which a mismatched oligonucleotide phosphorothioate was studied showed no cleavage of RNA. Lane (−) shows that in presence of RNase H, RNA was not cleaved.

EXAMPLE 5

Inhibition of HIV by Hybrid Oligonucleotide Phosphorothioates

Hybrid oligonucleotide phosphorothioates were tested for their ability to inhibit HIV-1 in tissue culture. H9 lymphocytes were infected with HIV-1 virions (≡0.01–0.1 $TCID_{50}$/ cell) for one hour at 37° C. After one hour, unadsorbed virions were washed and the infected cells were divided among wells of 24 well plates. To the infected cells, an appropriate concentration (from stock solution) of oligonucleotide was added to obtain the required concentration in 2 ml medium. The cells were then cultured for four days. At the end of four days, level of HIV-1 expression was measured by synthetic formation, p. 24 expression and reverse transcriptase activity. The level of expression of −24 was compared between oligonucleotide treated and untreated (no drug) infected cells. (Table IV)

All of the hybrid oligonucleotide phosphorothioates tested showed significant inhibition of syncytia formation, p24 expression and reverse transcriptase, without significant cytotoxicity. These results indicate that hybrid oligonucleotide phosphorothioates containing 2'-OMe ribonucleotides are more effective as inhibitors of gene expression compared to oligonucleotide phosphorothioates. Similar effectiveness would be expected for hybrid oligonucleotide phosphorothioates and/or phosphorodithioates containing ribonucleosides, 2'-substituted ribonucleosides, or a mixture of ribonucleosides and 2'-substituted ribonucleosides. The activity of compounds listed in Table III are listed in Table IV below.

TABLE IV

Anti-HIV activity of oligonucleotides (listed in TABLE III)

| Oligonucleotides | Syncytia formed | Inhibition of p24 (%) | Inhibition of Reverse Transcriptase (%) |
|---|---|---|---|
| Oligo A (SEQ ID NO:1) | ++ | 93 | 88 |
| Oligo B (SEQ ID NO:2) | ++ | 95 | 97 |
| Oligo C (SEQ ID NO:3) | + | 98 | 97 |
| Oligo D (SEQ ID NO:4) | + | 98 | 83 |
| Oligo E (SEQ ID NO:5) | +++ | 90 | 94 |
| Oligo F (SEQ ID NO:6) | +++ | 88 | 91 |
| + Control | ++++ | | |
| − Control | — | | |

+ Control = HIV-1 Infected cells without oligonucleotides
− Control = Uninfected cells without oligonucleotides
1. Number of Syncytia formed in oligonucleotide treated cells were compared with the number of syncytia formed in untreated infected cells.
2. Inhibition is compared to untreated infected cells.

We claim:

1. A hybrid antisense oligonucleotide that is complementary to a single stranded target nucleic acid and inhibits expression of the target nucleic acid, the hybrid antisense oligonucleotide comprising at least four contiguous deoxyribonucleotides and at least two 2'-O-methyl-substituted ribonucleotides at the 3'-end of the oligonucleotide, and further comprising one or more phosphorothioate internucleotide linkages.

2. The hybrid antisense oligonucleotide according to claim 1, wherein the internucleotide linkages of the oligonucleotide further comprises one or more phosphodiester linkages.

3. The hybrid antisense oligonucleotide according to claim 1, further comprising at least two 2'-O-methyl-substituted ribonucleotides at the 5'-end.

4. The hybrid antisense oligonucleotide according to claim 2, further comprising at least two 2'-O-methyl-substituted ribonucleotides at the 5'-end.

5. The hybrid antisense oligonucleotide according to claim 1, wherein the deoxyribonucleotides are present in a segment of at least four contiguous deoxyribonucleotides.

6. The hybrid antisense oligonucleotide according to claim 3, wherein the deoxyribonucleotides are present in a segment of at least four contiguous deoxyribonucleotides.

7. The hybrid antisense oligonucleotide according to claim 4, further comprising a segment of at least four contiguous deoxyribonucleotides.

8. The hybrid antisense oligonucleotide according to claim 1, wherein the deoxyribonucleotides are connected by phosphorothioate internucleotide linkages.

9. The hybrid antisense oligonucleotide according to claim 5, wherein the deoxyribonucleotides are connected by phosphorothioate internucleotide linkages.

10. The hybrid antisense oligonucleotide according to claim 7, wherein the deoxyribonucleotides are connected by phosphorothioate internucleotide linkages.

11. The hybrid antisense oligonucleotide according to claim 1, wherein the 3'-terminal 2'-O-methyl-substituted ribonucleotides are connected by phosphorothioate internucleotide linkages.

12. The hybrid antisense oligonucleotide according to claim 5, wherein the 3'-terminal 2'-O-methyl-substituted ribonucleotides are connected by phosphorothioate internucleotide linkages.

13. The hybrid antisense oligonucleotide according to claim 7, wherein the 3'-terminal 2'-O-methyl-substituted ribonucleotides are connected by phosphorothioate internucleotide linkages.

14. The hybrid antisense oligonucleotide according to claim 1, wherein the ribonucleotides are connected by phosphorothioate internucleotide linkages.

15. The hybrid antisense oligonucleotide according to claim 5, wherein the ribonucleotides are connected by phosphorothioate internucleotide linkages.

16. The hybrid antisense oligonucleotide according to claim 7, wherein the ribonucleotides are connected by phosphorothioate internucleotide linkages.

17. An oligonucleotide according to claim 1 comprising from about 6 to about 50 nucleotides.

18. An oligonucleotide according to claim 1 comprising from about 6 to about 50 nucleotides.

19. An oligonucleotide according to claim 5 comprising from about 6 to about 50 nucleotides.

20. An oligonucleotide according to claim 7 comprising from about 6 to about 50 nucleotides.

21. An oligonucleotide according to claim 16 wherein the target nucleic acid is a nucleic acid from a virus.

22. An oligonucleotide according to claim 19 wherein the target nucleic acid is a nucleic acid from a virus.

23. An oligonucleotide according to claim 20 wherein the target nucleic acid is a nucleic acid from a virus.

24. An oligonucleotide according to claim 21 wherein the target nucleic acid is a nucleic acid from HIV.

25. An oligonucleotide according to claim 22 wherein the target nucleic acid is a nucleic acid from HIV.

26. An oligonucleotide according to claim 23 wherein the target nucleic acid is a nucleic acid from HIV.

27. A hybrid antisense oligonucleotide that is complementary to a single stranded target nucleic acid and inhibits expression of the target nucleic acid, the hybrid antisense oligonucleotide comprising at least three contiguous deoxyribonucleotides and at least two 2'-O-alkoxyalkyl-substituted ribonucleotides at the 3'-end of the oligonucleotide, and further comprising one or more phosphorothioate internucleotide linkages.

28. The hybrid antisense oligonucleotide according to claim 27, wherein the internucleotide linkages of the oligonucleotide further comprises one or more phosphodiester linkages.

29. The hybrid antisense oligonucleotide according to claim 27, further comprising at least two 2'-O-alkoxyalkyl-substituted ribonucleotides at the 5'-end.

30. The hybrid antisense oligonucleotide according to claim 28, further comprising at least two 2'-O-alkoxyalkyl-substituted ribonucleotides at the 5'-end.

31. The hybrid antisense oligonucleotide according to claim 27, wherein the deoxyribonucleotides are present in a segment of at least four contiguous deoxyribonucleotides.

32. The hybrid antisense oligonucleotide according to claim 29, wherein the deoxyribonucleotides are present in a segment of at least four contiguous deoxyribonucleotides.

33. The hybrid antisense oligonucleotide according to claim 30, further comprising a segment of at least four contiguous deoxyribonucleotides.

34. The hybrid antisense oligonucleotide according to claim 27, wherein the deoxyribonucleotides are connected by phosphorothioate internucleotide linkages.

35. The hybrid antisense oligonucleotide according to claim 31, wherein the deoxyribonucleotides are connected by phosphorothioate internucleotide linkages.

36. The hybrid antisense oligonucleotide according to claim 33, wherein the deoxyribonucleotides are connected by phosphorothioate internucleotide linkages.

37. The hybrid antisense oligonucleotide according to claim 27, wherein the 3'-terminal 2'-O-alkoxyalkyl-substituted ribonucleotides are connected by phosphorothioate internucleotide linkages.

38. The hybrid antisense oligonucleotide according to claim 31, wherein the 3'-terminal 2'-O-alkoxyalkyl-substituted ribonucleotides are connected by phosphorothioate internucleotide linkages.

39. The hybrid antisense oligonucleotide according to claim 33, wherein the 3'-terminal 2'-O-alkoxyalkyl-substituted ribonucleotides are connected by phosphorothioate internucleotide linkages.

40. The hybrid antisense oligonucleotide according to claim 27, wherein the ribonucleotides are connected by phosphorothioate internucleotide linkages.

41. The hybrid antisense oligonucleotide according to claim 31, wherein the ribonucleotides are connected by phosphorothioate internucleotide linkages.

42. The hybrid antisense oligonucleotide according to claim 33, wherein the ribonucleotides are connected by phosphorothioate internucleotide linkages.

43. The oligonucleotide according to claim 27 comprising from about 6 to about 50 nucleotides.

44. The oligonucleotide according to claim 27 comprising from about 6 to about 50 nucleotides.

45. The oligonucleotide according to claim 31 comprising from about 6 to about 50 nucleotides.

46. The oligonucleotide according to claim 33 comprising from about 6 to about 50 nucleotides.

47. The oligonucleotide according to claim 44 wherein the target nucleic acid is a nucleic acid from a virus.

48. The oligonucleotide according to claim 45 wherein the target nucleic acid is a nucleic acid from a virus.

49. The oligonucleotide according to claim 46 wherein the target nucleic acid is a nucleic acid from a virus.

50. The oligonucleotide according to claim 47 wherein the target nucleic acid is a nucleic acid from HIV.

51. The oligonucleotide according to claim 48 wherein the target nucleic acid is a nucleic acid from HIV.

52. The oligonucleotide according to claim 49 wherein the target nucleic acid is a nucleic acid from HIV.

53. The oligonucleotide according to any one of claims 27 to 52 wherein the alkoxyalkyl moiety is methoxyethyl.

* * * * *